United States Patent
Vega et al.

(10) Patent No.: US 6,172,108 B1
(45) Date of Patent: Jan. 9, 2001

(54) HYDRAZIDE COMPOUNDS

(75) Inventors: Antonio Monge Vega, Cizur Menor; Ignacio Aldana Moraza, Pamplona, both of (ES); Daniel-Henri Caignard, Le Pecq (FR); Jacques Duhault, Croissy sur Seine (FR); Jean Boutin, Suresnes (FR); Odile Dellazuana, Romainville (FR)

(73) Assignee: Adir et Compagnie, Courbevoie (FR)

( * ) Notice: Under 35 U.S.C. 154(b), the term of this patent shall be extended for 0 days.

(21) Appl. No.: 09/464,182

(22) Filed: Dec. 16, 1999

(30) Foreign Application Priority Data

Dec. 17, 1998 (ES) .................................................. 9802626

(51) Int. Cl.$^7$ .......................... A61K 31/27; A61K 31/18; C07C 271/02; C07C 313/00; C07C 243/00
(52) U.S. Cl. .......................... 514/485; 514/486; 514/488; 514/601; 514/602; 514/603; 514/604; 514/614; 514/615; 560/29; 560/31; 560/32; 564/81; 564/101; 564/148; 564/149; 564/150; 564/151
(58) Field of Search ................................. 560/29, 31, 32; 564/81, 101, 148, 149, 150, 151; 514/485, 486, 488, 601, 602, 603, 604, 614, 615

(56) References Cited

U.S. PATENT DOCUMENTS 4,031,127 * 6/1977 Leone et al. .......................... 260/465
5,030,547 * 7/1991 Katoh et al. .......................... 430/264

OTHER PUBLICATIONS

Braichenko et al, N–aryl–beta–amino acid. III N–aryl–sulfonyl–beta–alanine hydrazides Khim. —Farm. Zh. 6(8), pp. 6–8, 1972.*

* cited by examiner

Primary Examiner—Mukund J. Shah
Assistant Examiner—Ben Schroeder
(74) Attorney, Agent, or Firm—The Firm of Hueschen and Sage

(57) ABSTRACT

Compounds of formula (I):

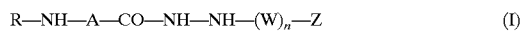

$$R-NH-A-CO-NH-NH-(W)_n-Z \quad (I)$$

wherein:
n is 0 or 1,
W represents —CO— or $S(O)_r$ wherein r is 0, 1 or 2,
Z represents a group selected from aryl, arylalkyl, heteroaryl and heteroarylalkyl, each optionally substituted,
R represents a grouping selected from:

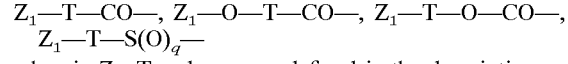

$Z_1$—T—CO—, $Z_1$—O—T—CO—, $Z_1$—T—O—CO—, $Z_1$—T—$S(O)_q$— wherein $Z_1$, T and q are as defined in the description,
A represents alkylene, alkenylene or alkynylene each having from 3 to 8 carbon atoms, alkylenecycloalkylene, cycloalkylenealkylene, alkylenecycloalkylenealkylene, alkylenearylene, arylenealkylene, alkylenearylenealkylene a grouping

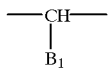

wherein
$B_1$ is as defined in the description, or A forms with the adjacent nitrogen atom a grouping

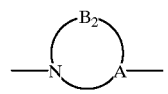

as defined in the description, and
medicinal products containing the same which are useful as Neuropeptide Y receptors ligands.

18 Claims, No Drawings

HYDRAZIDE COMPOUNDS

DESCRIPTION OF THE PRIOR ART

Hydrazide compounds have been described in the literature (J. Org. Chem., 1971, 36, 1580) although no pharmacological property has been mentioned. Other compounds of related structure are used in the composition of photographic films (JP 02008833), or have been used in the formation of polymers that are used to prepare semipermeable membranes (J. Appl. Polym. Sci., 1992, 44, 1383).

The compounds of the present invention have a novel structure which imparts to them great affinity for neuropeptide Y receptors.

Ligands of those receptors have been described recently. By way of example, there may be mentioned cyclic peptide compounds (WO 9400486), amino acid compounds of arginine (WO 9417035), or non-peptide compounds having a guanidine group (EP 448765, J. Med. Chem., 1994, 37, 2242).

BACKGROUND OF THE INVENTION

Neuropeptide Y (NPY) is a peptide of 36 amino acids, related to the peptide YY (PYY) and to pancreatic polypeptides (PP). Originally isolated from pig brain (Proc. Natl. Acad. Sci., 1982, 79, 5485), NPY is widely distributed in mammals at the level of the central and peripheral nervous systems. This neurotransmitter is present in high concentrations in nerve fibres of the brain, but also of the heart, the sympathetic ganglia, blood vessels and smooth muscles of the vas deferens and of the gastrointestinal tract. It is responsible for various physiological effects which are exerted via the intermediary of specific receptors (Y). The latter form a heterogeneous group, 6 sub-types of which have been identified to date: $Y_1$ to $Y_6$ (Pharmacological Reviews, 1998, 50, 143). NPY is involved in eating behaviour by strongly stimulating food intake (Proc. Natl. Acad. Sci., 1985, 82, 3940) or by exerting a regulatory role on the HPA (hypothalamic-pituitary-adrenal) axis (J. of Neuroendocrinol., 1995, 7, 273). It also exhibits anxiolytic and sedative properties (Neuropsycho-pharmacology, 1993, 8, 357), a strong vasoconstrictive ability (Eur. J. Pharmacol., 1984, 85, 519) which induces an increase in blood pressure, and also has an effect on the circadian rhythm (Neuroscience and biobehavioral reviews, 1995, 19, 349). In addition to the fact that the compounds of the invention are new, they have a structure which imparts to them great affinity for NPY receptors. It will thus be possible to use them in the treatment of pathologies in which an NPY receptor ligand is necessary, especially in the treatment of pathologies associated with eating behaviour disorders or energy balance disorders, such as diabetes, obesity, bulimia, anorexia nervosa, and also in the treatment of arterial hypertension, anxiety, depression, epilepsy, sexual dysfunctions and sleep disorders.

DETAILED DESCRIPTION OF THE INVENTION

The present invention relates to compounds of formula (I):

$$R-NH-A-CO-NH-NH-(W)_n-Z \quad (I)$$

wherein:

n is 0 or 1,

W represents a —CO— group or an S(O)r group wherein r is 0, 1 or 2,

Z represents a group selected from optionally substituted aryl, optionally substituted arylalkyl, optionally substituted heteroaryl and optionally substituted heteroarylalkyl, R represents a group selected from:
- $Z_1$—T—CO—
- $Z_1$—O—T—CO—
- $Z_1$—T—O—CO—
- $Z_1$—T—S(O)$_q$— wherein:

$Z_1$ represents an optionally substituted aryl, optionally substituted arylalkyl, optionally substituted heteroaryl or optionally substituted heteroarylalkyl group, T represents a σ bond or an alkylene, alkenylene or alkynylene group, q represents an integer 0, 1 or 2, A represents a linear or branched alkylene group having from 3 to 8 carbon atoms, a linear or branched alkenylene group having from 3 to 8 carbon atoms, a linear or branched alkynylene group having from 3 to 8 carbon atoms, an alkylenecycloalkylene group, a cycloalkylenealkyene group, an alkylenecycloalkylenealkylene group, an alkylenearylene group, an arylenealkylene group, an alkylenearylenealkylene group, a grouping $$-\underset{\underset{B_1}{|}}{CH}-$$

wherein $B_1$ represents an optionally substituted aryl, optionally substituted arylalkyl, optionally substituted heteroaryl or optionally substituted heteroarylalkyl group, or A forms with the nitrogen atom a grouping wherein $B_2$ represents a saturated or unsaturated mono- or bi-cyclic system having from 5 to 11 ring members, optionally containing from 1 to 3 additional hetero atoms selected from nitrogen, oxygen and sulphur, with the proviso that when simultaneously n is 0, A represents a grouping $$-\underset{\underset{B_1}{|}}{CH}-,$$

$B_1$ being a benzyl group, and Z represents an optionally substituted phenyl group, then R is other than a benzoyl group, their enantiomers, diastereoisomers, and addition salts thereof with a pharmaceutically acceptable acid or base, it being understood that:

the term "alkyl" denotes a linear or branched group having from 1 to 6 carbon atoms, the term "alkylene" denotes a linear or branched bivalent radical containing from 1 to 6 carbon atoms, unless indicated otherwise, the term "alkenylene" denotes a linear or branched bivalent radical containing from 2 to 6 carbon atoms and from 1 to 3 double bonds, unless indicated otherwise, the term "alkynylene" denotes a linear or branched bivalent radical containing from 2 to 6 carbon atoms and from 1 to 3 triple bonds, unless indicated otherwise, the term "aryl" denotes a phenyl, naphthyl, dihydronaphthyl or tetrahydronaphthyl group, and the term "arylene" denotes a bivalent radical of the same type, the term "heteroaryl" denotes an unsaturated or partially unsaturated mono- or bi-cyclic group having from 5 to 11 ring members, containing from 1 to 4 hetero atoms selected from nitrogen, oxygen and sulphur, the term "alkylenecycloalkylene" represents a grouping —$A_1$—$A_2$—, the term "cycloalkylene-alkylene" represents a grouping —$A_2$—$A_1$—, and the term "alkylenecycloalkylenealkylene" represents a grouping —$A_1$—$A_2$—$A_1$, the term "alkylenearylene" represents a grouping —$A_1$—$A_3$—, the term "arylenealkylene" represents a grouping —$A_3$—$A_1$—, the term "alkylenearylenealkylene" represents a grouping —$A_1$—$A_3$—$A_1$—, wherein Al is an alkylene group as defined hereinbefore, $A_2$ is a ($C_4$–$C_8$)cycloalkylene group, and $A_3$ is an arylene group as defined hereinbefore, the expression "optionally substituted" applied to the terms "aryl", "arylalkyl", "heteroaryl" and "heteroarylalkyl" indicates that those groups are substituted on their cyclic moiety by from 1 to 5 identical or different substituents selected from linear or branched ($C_1$–$C_6$)alkyl, linear or branched ($C_1$–$C_6$)alkoxy, halogen, hydroxy, perhalo-($C_1$–$C_6$)alkyl in which the alkyl moiety is linear or branched, nitro, linear or branched ($C_1$–$C_6$)acyl, linear or branched ($C_1$–$C_6$)alkylsulphonyl, and amino (amino optionally being substituted by one or two linear or branched ($C_1$–$C_6$)alkyl and/or linear or branched ($C_1$–$C_6$) acyl groups).

Among the pharmaceutically acceptable acids, there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases, there may be mentioned by way of non-limiting example sodium hydroxide, potassium hydroxide, triethylamine, tert-butylamine, etc.

Advantageously, the invention relates to compounds of formula (I) wherein R represents a grouping $Z_1$—T—CO, $Z_1$ preferably being an optionally substituted aryl group, and T preferably being an alkylene group or a bond.

Another advantageous aspect of the invention relates to compounds of formula (I) wherein R represents a grouping $Z_1$—O—T—CO, $Z_1$ preferably being an optionally substituted aryl group, and T preferably being an alkylene group or a bond.

Another advantageous aspect of the invention relates to compounds of formula (I) wherein R represents a grouping $Z_1$—T—O—CO, $Z_1$ preferably being an optionally substituted aryl group, and T preferably being an alkylene group or a bond.

Another advantageous aspect of the invention relates to compounds of formula (I) wherein R represents a grouping $Z_1$—T—S(O)$_q$—, $Z_1$ preferably being an optionally substituted aryl group, and T preferably being an alkylene group or a bond, and q preferably being 2.

The preferred aryl group are phenyl or naphthyl.

Preferred compounds of the invention are those wherein W represents a —CO— group.

Other preferred compounds of the invention are those wherein W represents an $SO_2$ group.

In the preferred compounds of the invention, Z represents a group selected from optionally substituted aryl and optionally substituted heteroaryl.

Preferred compounds of the invention are those wherein A represents a grouping

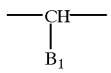

wherein $B_1$ is an optionally substituted arylalkyl group (for example a benzyl or tolylmethyl group).

Other preferred compounds of the invention are those wherein A represents an alkylene-cycloalkylene group (for example methylenecyclohexylene).

Other preferred compounds of the invention are those wherein A represents an alkylenearylene group (for example methylenephenylene).

In the compounds of the invention, the cyclic groupings

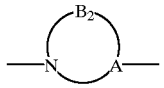

are advantageously selected from pyrrolidine, perhydroindole and piperidine groups.

In an especially advantageous manner, the invention relates to compounds of formula (I) wherein W represents a —CO— group, Z represents a group selected from optionally substituted aryl and optionally substituted heteroaryl, R represents a grouping selected from $Z_1$—T—CO—, $Z_1$—O—T—CO—, $Z_1$—T—O—CO— and $Z_1$—T—S(O)$_q$— wherein $Z_1$ is preferably an optionally substituted aryl or optionally substituted heteroaryl group, T represents an alkylene group (for example methylene), and q is 2, and A represents an alkylene-cycloalkylene group, a grouping

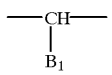

wherein B, is an optionally substituted arylalkyl group,or A forms with the adjacent nitrogen atom a pyrrolidine, perhydroindole or piperidine group.

Among the preferred compounds of the invention, there may be mentioned:
—N2-({4-[(2-benzoylhydrazino)carbonyl] cyclohexyl}methyl)-2-naphthalenesulphonamide
—N1-({4-[(2-benzoylhydrazino)carbonyl] cyclohexyl}methyl)-1-(2-nitrobenzene)-sulphonamide
—N1-[1-benzyl-2-oxo-2-(2-phenylhydrazino)ethyl]-1-(4-chlorobenzene)sulphonamide.

The present invention relates also to a process for the preparation of compounds of formula (I), characterised in that there is used as starting material a compound of formula (II):

wherein A is as defined for formula (I),
which is condensed in a basic medium with a halogen compound of formula (III):

wherein R is as defined for formula (I),
to yield a compound of formula (IV):

wherein R and A are as defined hereinbefore,
which compound (IV) is condensed, in the presence of a coupling agent, with a monosubstituted hydrazine of formula (V),

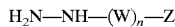

wherein n, W and Z are as defined for formula (I),
to yield compounds of formula (I):

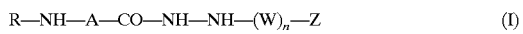

wherein R, A, n, W and Z are as defined hereinbefore,
which compound of formula (I):
may be purified, if necessary, according to a conventional purification technique,
is separated, where appropriate, into its isomers according to a conventional separation technique,
is converted, if desired, into an addition salt thereof with a pharmaceutically acceptable acid or base.

The present invention relates also to pharmaceutical compositions comprising as active ingredient at least one compound of formula (I), on its own or in combination with one or more inert non-toxic excipients or carriers.

Among the pharmaceutical compositions according to the invention, there may be mentioned more especially those that are suitable for oral, parenteral or nasal administration, tablets or dragées, sublingual tablets, gelatin capsules, lozenges, suppositories, creams, ointments, dermal gels, etc.

The useful dosage varies according to the age and weight of the patient, the nature and severity of the disorder and the route of administration, which may be oral, nasal, rectal or parenteral. Generally the unit dose ranges from 0.05 to 500 mg for a treatment in from 1 to 3 administrations per 24 hours.

The following Examples illustrate the invention but do not limit it in any way. The structures of the compounds described were confirmed by the usual spectroscopic techniques. The starting materials used are known products or are prepared according to known procedures.

EXAMPLE 1
Benzyl N-[1-benzyl-2-oxo-2-(2-phenylhydrazino)ethyl]carbamate

Step a: 2-Benzyloxycarbonylamino-3-phenylpropanoic acid 82 mmol (13.9 g) of benzyl chloroformate and 20 ml of 4M aqueous sodium hydroxide are added over a period of 30 minutes to a solution, cooled to 0° C., of 80 mmol (13.2 g) of phenylalanine in 20 ml of 4M aqueous sodium hydroxide. The solution returns to room temperature during a period of 1 hour. The reaction mixture is extracted with ether. The aqueous phase is rendered acidic to pH=2 with a dilute hydrochloric acid solution. The precipitate that forms is filtered off and washed to yield the expected compound.

Step b: Benzyl N-[1-benzyl-2-oxo-2-(2-phenylhydrazino)ethyl]carbamate 3.25 mmol (0.63 g) of EDC are added to a solution, cooled to 0° C., of 2.85 mmol (0.8 g) of the compound described in the preceding Step and 3.25 mmol (0.43 g) of HOBT in 20 ml of dichloromethane. The reaction mixture is stirred at 0° C. for 1 hour and then 3.25 mmol (0.32 ml) of phenylhydrazine are added. The reaction mixture is stirred at 0° C. for 1 hour, and then at room temperature for 24 hours. The reaction mixture is filtered and the filtrate is concentrated. The resulting residue is taken up in ether (15 ml) and 10 ml of water are added. The resulting precipitate is filtered off, and washed with water and then with ether to yield the expected compound.

Melting point: 175–177° C.
Elemental microanalysis:

|  | C | H | N |
|---|---|---|---|
| % calculated | 70.95 | 5.91 | 10.79 |
| % found | 71.27 | 5.90 | 10.71 |

EXAMPLE 2
Benzyl N-[2-(2-benzoylhydrazino)-1-benzyl-2-oxoethyl]carbamate

The expected product is obtained according to the process described in Example 1, in Step b replacing phenylhydrazine by phenylhydrazide.

Melting point: 172–174° C.
Elemental microanalysis:

|  | C | H | N |
|---|---|---|---|
| % calculated | 69.06 | 5.52 | 10.07 |
| % found | 69.14 | 5.71 | 9.92 |

EXAMPLE 3
Benzyl N-[1-benzyl-2-oxo-2-(2-nicotinoylhydrazino)ethyl]carbamate

The expected product is obtained according to the process described in Example 1, in Step b replacing phenylhydrazine by 3-pyridinecarbohydrazide.

Elemental microanalysis:

|  | C | H | N |
|---|---|---|---|
| % calculated | 66.03 | 5.26 | 13.40 |
| % found | 66.00 | 5.72 | 13.68 |

EXAMPLE 4
Benzyl N-{1-benzyl-2-[2-(3-indolyl)acetyl]-2-oxoethyl}carbamate

The expected product is obtained according to the process described in Example 1, in Step b replacing phenylhydrazine by 3-indolylacetohydrazide.

Elemental microanalysis

|  | C | H | N |
|---|---|---|---|
| % calculated | 68.94 | 5.53 | 11.91 |
| % found | 69.23 | 5.81 | 11.57 |

EXAMPLE 5
N1-[1-Benzyl-2-oxo-2-(2-phenylhydrazino)ethyl]-2-phenoxyacetamide

Step a: 2-[(2-Phenoxyacetyl)amino]-3-phenylpropanoic acid

A solution of 6.6 mmol (1.0 g) of phenoxyacetic acid in 15 ml of dioxane is treated with 49.3 mmol (3.6 ml) of thionyl chloride. The reaction mixture is stirred at room temperature for 2 hours and then concentrated. The residue, taken up in 10 ml of dichloromethane, and 7.9 mmol (0.3 g) of sodium hydroxide in 10 ml of water are added in succession to a solution of 7.6 mmol (1.25 g) of phenylalanine and 7.6 mmol (0.3 g) of sodium hydroxide in 10 ml of water, the temperature being maintained at 10° C. The reaction mixture is then stirred for 1 hour at room temperature. After decanting, the aqueous phase is washed with dichloromethane, and then rendered acidic to pH=2 with a dilute hydrochloric acid solution. The precipitate that forms is filtered off and recrystallised from water to yield the expected product.

Step b: N1-[1-Benzyl-2-oxo-2-(2-phenylhydrazino)ethyl]-2-phenoxyacetamide 3.7 mmol (0.71 g) of EDC are added to a solution, cooled to 0° C., of 3.35 mmol (1 g) of the compound described in the preceding Step and 3.7 mmol (0.56 g) of HOBT in 15 ml of dichloromethane. After one hour at 0° C., a solution of 3.7 mmol (0.4 g) of phenylhydrazine in 10 ml of dichloromethane is added. The reaction mixture is stirred at 0° C. for 1 hour and then at room temperature for 24 hours. The organic phase is washed with water, dried over sodium sulphate and concentrated. The resulting residue is washed in ether and then filtered to yield the expected compound.

Melting point: 172–175° C.

Elemental microanalysis:

|  | C | H | N |
|---|---|---|---|
| % calculated | 70.95 | 5.91 | 10.80 |
| % found | 70.91 | 6.06 | 10.68 |

EXAMPLE 6

N1-[2-(2-Benzoylhydrazino)-1-benzyl-2-oxoethyl]-2-phenoxyacetamide

The expected product is obtained according to the process described in Example 5, in Step b replacing phenylhydrazine by phenylhydrazide.

Elemental microanalysis:

|  | C | H | N |
|---|---|---|---|
| % calculated | 69.06 | 5.12 | 10.07 |
| % found | 68.88 | 5.52 | 9.84 |

EXAMPLE 7

N1-{1-Benzyl-2-[2-(2-indolylcarbonyl)hydrazino]-2-oxoethyl}-2-phenoxyacetamide

The expected product is obtained according to the process described in Example 5, in Step b replacing phenylhydrazine by 2-indolecarbohydrazide.

Elemental microanalysis:

|  | C | H | N |
|---|---|---|---|
| % calculated | 68.42 | 5.26 | 12.28 |
| % found | 67.97 | 5.44 | 12.42 |

EXAMPLE 8

N1-[1-Benzyl-2-oxo-2-(2-nicotinoylhydrazino)ethyl]-2-phenoxyacetamide

The expected product is obtained according to the process described in Example 5, in Step b replacing phenylhydrazine by 3-pyridinecarbohydrazide.

Elemental microanalysis:

|  | C | H | N |
|---|---|---|---|
| % calculated | 64.29 | 5.36 | 12.50 |
| % found | 64.06 | 5.34 | 12.34 |

EXAMPLE 9

N2-[1-Benzyl-2-oxo-2-(2-phenylhydrazino)ethyl]-2-indole carboxamide

Step a: 2-(2-Indolylcarbonylamino)-3-phenylpropanoic acid

The expected product is obtained according to the process described in Example 5, Step a, replacing phenoxyacetic acid by 2-indolecarboxylic acid.

Step b: N2-[1-Benzyl-2-oxo-2-(2-phenylhydrazino)ethyl]-2-indolecarboxamide

The expected product is obtained according to the process described in Example 5, Step b, using the compound described in the preceding Step as starting material.

Elemental microanalysis:

|  | C | H | N |
|---|---|---|---|
| % calculated | 72.36 | 5.53 | 14.07 |
| % found | 72.05 | 5.82 | 14.60 |

EXAMPLE 10

N2-[1-Benzyl-2-oxo-2-(2-phenylhydrazino)ethyl]-2-naphthalene sulphonamide

Step a: 2-[(2-Naphthylsulphonyl)amino]-3-phenylpropanoic acid

A solution of 7.6 mmol (1.71 g) of 2-naphthylsulphonyl chloride in 10 ml of dichloro-methane and a solution of 7.9 mmol (0.32 g) of sodium hydroxide in 10 ml of water are added slowly in succession to 7.6 mmol (1.25 g) of phenylalanine and 7.6 mmol (0.3 g) of sodium hydroxide in 10 ml of water. The reaction mixture is stirred for 1 hour at room temperature. After decanting, the aqueous phase is washed with dichloromethane and rendered acidic to pH=2 with a dilute hydrochloric acid solution. After extraction with dichloromethane, the organic phase is dried over sodium sulphate and concentrated to yield the expected product.

Step b: N2-[1-Benzyl-2-oxo-2-(2-phenylhydrazino)ethyl]-2-naphthalene-sulphonamide The expected product is obtained according to the process described in Example 1, Step b, using the compound described in the preceding Step as starting material.

Elemental microanalysis:

|  | C | H | N |
|---|---|---|---|
| % calculated | 67.41 | 5.17 | 9.44 |
| % found | 67.03 | 5.34 | 9.57 |

EXAMPLE 11
N2-[2-(2-Benzoylhydrazino)-1-benzyl-2-oxoethyl]-2-naphthalene-sulphonamide The expected product is obtained according to the process described in Example 1, Step b, using the compound described in Example 10, Step a, as starting material, and replacing phenylhydrazine by phenylhydrazide.

Melting point: 239–240° C.

Elemental microanalysis:

|  | C | H | N |
|---|---|---|---|
| % calculated | 65.96 | 4.86 | 8.87 |
| % found | 65.55 | 4.99 | 8.88 |

EXAMPLE 12
N2-[1-Benzyl-2-oxo-2-(2-phenylhydrazinoethyl]-2-naphthylamide

The expected product is obtained according to the process described in Example 1, in Step a replacing benzyl chloroformate by naphthoyl chloride.

Elemental microanalysis:

|  | C | H | N |
|---|---|---|---|
| % calculated | 76.28 | 5.62 | 10.27 |
| % found | 76.25 | 5.76 | 10.03 |

EXAMPLE 13
N2-[2-(2-Benzoylhydrazino)-1-benzyl-2-oxoethyl]-2-naphthylamide

The expected product is obtained according to the process described in Example 1, in Step a replacing benzyl chloroformate by naphthoyl chloride, and in Step b replacing phenyl-hydrazine by phenylhydrazide.

Elemental microanalysis:

|  | C | H | N |
|---|---|---|---|
| % calculated | 74.17 | 5.26 | 9.61 |
| % found | 74.21 | 5.38 | 9.49 |

EXAMPLE 14
N2-[1-Benzyl-2-oxo-2-(2-nicotinoylhydrazino)ethyl]-2-naphthylamide The expected product is obtained according to the process described in Example 1, in Step a replacing benzyl chloroformate by naphthoyl chloride, and in Step b replacing phenyl-hydrazine by 3-pyridinecarbohydrazide.

Elemental microanalysis:

|  | C | H | N |
|---|---|---|---|
| % calculated | 71.23 | 5.02 | 12.79 |
| % found | 70.97 | 5.38 | 12.61 |

EXAMPLE 15
N2-{1-Benzyl-2-[2-(2-indolecarbonyl)hydrazino]-2-oxoethyl}-2-naphthylamide The expected product is obtained according to the process described in Example 1, in Step a replacing benzyl chloroformate by naphthoyl chloride, and in Step b replacing phenyl-hydrazine by 2-indolecarbohydrazide.

Melting point: 214–215° C.

Elemental microanalysis:

|  | C | H | N |
|---|---|---|---|
| % calculated | 73.11 | 5.25 | 11.76 |
| % found | 72.98 | 5.16 | 11.75 |

EXAMPLE 16
N1-[1-Benzyl-2-oxo-2-(2-phenylhydrazino)ethyl]-1-benzene-sulphonamide Step a: 2-(Phenylsulphonylamino)-3-phenylpropanoic acid A mixture of 151 mmol (26.6 g) of benzenesulphonyl chloride and 50 ml of 4M aqueous sodium hydroxide is added to a solution of 37.8 mmol (6.25 g) of phenylalanine in 50 ml of 4M aqueous sodium hydroxide. The reaction mixture is stirred at room temperature for 24 hours. The solution is then rendered acidic to pH=2 with dilute hydrochloric acid and extracted with ether. The organic phase is dried over magnesium sulphate and concentrated. The resulting residue is recrystallised from ethanol to yield the expected compound.

Step b: N1-[1-Benzyl-2-oxo-2-(2-phenylkydrazino)ethyl]-1-benzenesulphonamide

The expected product is obtained according to the process described in Example 1, Step b, using the compound described in the preceding Step as starting material.

Melting point: 162–163° C.

Elemental microanalysis:

|  | C | H | N |
|---|---|---|---|
| % calculated | 63.80 | 5.32 | 10.63 |
| % found | 63.03 | 5.38 | 10.38 |

EXAMPLE 17
N1-[2-(2-Benzoylhydrazino)-1-benzyl-2-oxoethyl]-1-benzene-sulphonamide The expected product is obtained according to the process described in Example 1, Step b, using the compound of Example 16, Step a, as starting material, and replacing phenyl-hydrazine by phenylhydrazide.

Melting point: 200° C.
Elemental microanalysis:

|  | C | H | N |
|---|---|---|---|
| % calculated | 62.41 | 4.96 | 9.93 |
| % found | 62.59 | 5.06 | 9.84 |

EXAMPLE 18
N1-[1-Benzyl-2-oxo-2-(2-phenylhydrazino)ethyl]-1-(4-chloro-benzene)sulphonamide The expected product is obtained according to the process described in Example 10, in Step a replacing 2-naphthylsulphonyl chloride by 4-chlorobenzenesulphonyl chloride.
Melting point: 174–1 75° C.
Elemental microanalysis:

|  | C | H | N |
|---|---|---|---|
| % calculated | 58.67 | 4.66 | 9.78 |
| % found | 58.63 | 4.77 | 9.70 |

EXAMPLE 19
N1-[2-(2-Benzoylhydrazino)-1-benzyl-2-oxoethyl]-1-(4-chloro-benzene)sulphonamide The expected product is obtained according to the process described in Example 10, in Step a replacing 2-naphthylsulphonyl chloride by 4-chlorobenzenesulphonyl chloride, and in Step b replacing phenylhydrazine by phenylhydrazide.
Melting point: 192–193° C.
Elemental microanalysis:

|  | C | H | N |
|---|---|---|---|
| % calculated | 57.70 | 4.37 | 9.18 |
| % found | 57.50 | 4.43 | 9.14 |

EXAMPLE 20
N1-[1-Benzyl-2-oxo-2-(2-phenylhydrazino)ethyl]-1-(3,4-dichloro-benzene)sulphonamide The expected product is obtained according to the process described in Example 16, in Step a replacing benzenesulphonyl chloride by 3,4-dichlorobenzenesulphonyl chloride.
Melting point: 164–165° C.
Elemental microanalysis:

|  | C | H | N |
|---|---|---|---|
| % calculated | 54.32 | 4.12 | 9.05 |
| % found | 54.14 | 4.16 | 8.87 |

EXAMPLE 21
N1-[2-(2-Benzoylhydrazino)-1-benzyl-2-oxoethyl-1-(3,4-dichloro-benzene)sulphonamide The expected product is obtained according to the process described in Example 16, in Step a replacing benzenesulphonyl chloride by 3,4-dichlorobenzenesulphonyl chloride, and in Step b replacing phenylhydrazine by phenylhydrazide.
Melting point: 200–201° C.
Elemental microanalysis:

|  | C | H | N |
|---|---|---|---|
| % calculated | 53.66 | 3.86 | 8.54 |
| % found | 53.45 | 3.93 | 8.28 |

EXAMPLE 22
Benzyl N-[1-(4-methoxybenzyl)-2-oxo-2-(2-phenylhydrazino)ethyl]-carbamate The expected product is obtained according to the process described in Example 1, in Step a replacing phenylalanine by O-methyltyrosine.
Melting point: 182–185° C.
Elemental microanalysis:

|  | C | H | N |
|---|---|---|---|
| % calculated | 68.74 | 5.97 | 10.02 |
| % found | 68.56 | 6.11 | 9.81 |

EXAMPLE 23
Benzyl N-[2-benzoylhydrazino-1-(4-methoxybenzyl) 2oxoethyl]carbamate The expected product is obtained according to the process described in Example 1, in Step a replacing phenylalanine by O-methyltyrosine, and in Step b replacing phenylhydrazine by phenylhydrazide.
Melting point: 208–209° C.
Elemental microanalysis:

|  | C | H | N |
|---|---|---|---|
| % calculated | 67.11 | 5.59 | 9.40 |
| % found | 67.19 | 5.74 | 9.32 |

EXAMPLE 24
Benzyl N-{2-[2-(24indolylcarbonyl)hydrazino]-1-(4-methoxybenzyl)-2-oxoethyl}carbamate The expected product is obtained according to the process described in Example 1, in Step a replacing phenylalanine by O-methyltyrosine, and in Step b replacing phenylhydrazine by 2-indolecarbohydrazide.
Melting point: 185–186° C.
Elemental microanalysis:

|  | C | H | N |
|---|---|---|---|
| % calculated | 66.67 | 5.35 | 11.52 |
| % found | 66.40 | 5.43 | 12.87 |

EXAMPLE 25
Benzyl N-[1-(4-methoxybenzyl)-2-(2-nicotinoylhydrazino)-2-oxoethyl]carbamate The expected product is obtained according to the process described in Example 1, in Step a replacing phenylalanine by O-methyltyrosine, and in Step b replacing phenylhydrazine by 3-pyridinecarbohydrazide.

Elemental microanalysis:

|  | C | H | N |
|---|---|---|---|
| % calculated | 64.29 | 5.36 | 12.50 |
| % found | 64.43 | 5.52 | 12.14 |

EXAMPLE 26
Benzyl N-(2-{2-[2-(3-indolyl)acetyl]hydrazino}-1-(4-methoxybenzyl)-2-oxoethyl)carbamate The expected product is obtained according to the process described in Example 1, in Step a replacing phenylalanine by O-methyltyrosine, and in Step b replacing phenylhydrazine by 3-indolylacetohydrazide.

Melting point: 194–195° C.

Elemental microanalysis:

|  | C | H | N |
|---|---|---|---|
| % calculated | 67.20 | 5.60 | 11.19 |
| % found | 67.01 | 5.59 | 11.12 |

EXAMPLE 27
N1-[1-(4-Methoxybenzyl)-2-oxo-2-(2-phenylhydrazino)ethyl]-2-phenoxyacetamide The expected product is obtained according to the process described in Example 5, in Step a replacing phenylalanine by O-methyltyrosine.

Elemental microanalysis:

|  | C | H | N |
|---|---|---|---|
| % calculated | 68.74 | 5.97 | 10.02 |
| % found | 68.37 | 6.06 | 9.86 |

EXAMPLE 28
N1-[2-(2-Benzoylhydrazino)-1-(4-methoxybenzyl)-2-oxoethyl]-2-phenoxyacetamide The expected product is obtained according to the process described in Example 5, in Step a replacing phenylalanine by O-methyltyrosine, and in Step b replacing phenylhydrazine by phenylhydrazide.

Elemental microanalysis:

|  | C | H | N |
|---|---|---|---|
| % calculated | 67.11 | 5.59 | 9.40 |
| % found | 67.19 | 5.81 | 9.60 |

EXAMPLE 29
N1-[1-(4-Methoxybenzyl)-2-(2-nicotinoylhydrazino)-2-oxoethyl]-2-phenoxyacetamide The expected product is obtained according to the process described in Example 5, in Step a replacing phenylalanine by O-methyltyrosine, and in Step b replacing phenylhydrazine by 3-pyridinecarbohydrazide.

Elemental microanalysis:

|  | C | H | N |
|---|---|---|---|
| % calculated | 64.29 | 5.36 | 12.50 |
| % found | 64.06 | 5.34 | 12.34 |

EXAMPLE 30
N2-[1-(4-Methoxybenzyl)-2-oxo-2-(2-phenylhydrazino)ethyl]-2-naphthalenesulphonamide The expected product is obtained according to the process described in Example 10, replacing phenylalanine by O-methyltyrosine.

Melting point: 210–212° C.

Elemental microanalysis:

|  | C | H | N |
|---|---|---|---|
| % calculated | 64.47 | 5.37 | 8.87 |
| % found | 64.17 | 5.25 | 8.56 |

EXAMPLE 31
N2-[2-(2-Benzoylhydrazino)-1-(4-methoxybenzyl)-2-oxoethyl]-2-naphthalenesulphonamide The expected product is obtained according to the process described in Example 10, in Step a replacing phenylalanine by O-methyltyrosine, and in Step b replacing phenylhydrazine by phenylhydrazide.

Melting point: 246–247° C.

Elemental microanalysis:

|  | C | H | N |
|---|---|---|---|
| % calculated | 63.28 | 5.07 | 8.20 |
| % found | 63.14 | 5.01 | 8.55 |

EXAMPLE 32
N2-[1-(4-Methoxybenzyl)-2-oxo-2-(2-phenylhydrazino)ethyl]-2-naphthylamide The expected product is obtained according to the process described in Example 1, in Step a replacing phenylalanine by O-methyltyrosine and benzyl chloroformate by naphthoyl chloride.

Elemental microanalysis:

|  | C | H | N |
|---|---|---|---|
| % calculated | 73.80 | 5.70 | 9.57 |
| % found | 73.53 | 5.62 | 9.54 |

EXAMPLE 33
N2-[1-(4-Methoxybenzyl)-2-(2-nicotinoylhydrazino)-2-oxoethyl]-2-naphthylamide The expected product is obtained according to the process described in Example 1, in Step a replacing phenylalanine by O-methyltyrosine and benzyl chloroformate by naphthoyl chloride, and in Step b replacing phenylhydrazide by 3-pyridinecarbohydrazide.

Elemental microanalysis:

|  | C | H | N |
|---|---|---|---|
| % calculated | 69.23 | 5.13 | 11.97 |
| % found | 69.25 | 5.13 | 11.72 |

EXAMPLE 34
N1-[1-(4-Methoxybenzyl)-2-oxo-2-(2-phenylhydrazino)ethyl]-1-benzenesulphonamide The expected product is obtained according to the process described in Example 16, in Step a replacing L-phenylalanine by O-methyltyrosine.

Melting point: 163–164° C.
Elemental microanalysis:

|  | C | H | N |
|---|---|---|---|
| % calculated | 62.12 | 5.41 | 9.88 |
| % found | 61.71 | 5.54 | 9.89 |

EXAMPLE 35
N1-[2-(2-Benzoylhydrazino)-1-(4-methoxybenzyl)-2-oxoethyl]-1-benzenesulphonamide The expected product is obtained according to the process described in Example 16, in Step a replacing L-phenylalanine by O-methyltyrosine, and in Step b replacing phenylhydrazine by phenylhydrazide.

Elemental microanalysis:

|  | C | H | N |
|---|---|---|---|
| % calculated | 60.85 | 5.07 | 6.26 |
| % found | 60.81 | 5.23 | 9.20 |

EXAMPLE 36
N1-[1-(4-Methoxybenzyl)-2-oxo-2-(2-phenylhydrazino)ethyl]-1-(4-chlorobenzene)sulphonamide The expected product is obtained according to the process described in Example 10, in Step a replacing phenylalanine by O-methyltyrosine and 2-naphthylsulphonyl chloride by 4-chlorobenzenesulphonyl chloride.

Melting point: 181–183° C.
Elemental microanalysis:

|  | C | H | N |
|---|---|---|---|
| % calculated | 56.31 | 4.92 | 9.39 |
| % found | 56.64 | 4.85 | 9.02 |

EXAMPLE 37
N1-[2-(2-Benzoylhydrazino)-1-(4-methoxybenzyl)-2-oxoethyl]-1-(4-chlorobenzene)sulphonamide The expected product is obtained according to the process described in Example 10, in Step a replacing phenylalanine by O-methyltyrosine and 2-naphthylsulphonyl chloride by 4-chlorobenzenesulphonyl chloride, and in Step b replacing phenylhydrazine by phenylhydrazide.

Elemental microanalysis:

|  | C | H | N |
|---|---|---|---|
| % calculated | 56.61 | 4.54 | 8.61 |
| % found | 56.82 | 4.55 | 8.61 |

EXAMPLE 38
N1-[1-(4-Methoxybenzyl)-2-oxo-2-(2-phenylhydrazino)ethyl]-1-(3,4-dichlorobenzene)sulphonamide The expected product is obtained according to the process described in Example 16, in Step a replacing phenylalanine by O-methyltyrosine and benzenesulphonyl chloride by 3,4-dichlorobenzenesulphonyl chloride.

Melting point: 153–154° C.
Elemental microanalysis:

|  | C | H | N |
|---|---|---|---|
| % calculated | 53.44 | 4.25 | 8.50 |
| % found | 53.80 | 4.38 | 8.30 |

EXAMPLE 39
N1-[2-(2-Benzoylhydrazino)-1-(4-methoxybenzyl)-2-oxoethyl]-1-(3,4-dichlorobenzene)sulphonamide The expected product is obtained according to the process described in Example 16, in Step a replacing phenylalanine by O-methyltyrosine and benzenesulphonyl chloride by 3,4-dichlorobenzenesulphonyl chloride, and in Step b replacing phenylhydrazine by phenyl-hydrazide.

Melting point: 214–215° C.
Elemental microanalysis:

|  | C | H | N |
|---|---|---|---|
| % calculated | 52.87 | 4.03 | 8.05 |
| % found | 52.60 | 4.09 | 8.17 |

EXAMPLE 40
N2-[6-Oxo-6-(2-phenylhydrazino)bexyl]-2-naphthalenesulphonamide

Step a: 6-[(2-Naphthylsulphonyl)amino]hexanoic acid 30.5 mmol (6.42 g) of 2-naphthylsulphonyl chloride and 15 ml of 4M aqueous sodium hydroxide are added in succession to a solution of 15.2 mmol (2 g) of 6-aminocaproic acid in 15 ml of 4M aqueous sodium hydroxide. The reaction mixture is stirred at room temperature for 24 hours. The solution is then rendered acidic to pH=2 with concentrated hydrochloric acid, and extracted with dichloromethane. The organic phase is dried over sodium sulphate and concentrated, and the resulting residue is recrystallised from hexane to yield the expected compound.

Step b: N2-[6-Oxo-6-(2-phenylhydrazino)hexyl]-2-naphthalenesulphonamide

The expected product is obtained according to the process described in Example 1, Step b, using the compound described in the preceding Step as starting material.

Elemental microanalysis:

|  | C | H | N |
|---|---|---|---|
| % calculated | 64.16 | 6.08 | 10.21 |
| % found | 64.23 | 5.88 | 9.95 |

EXAMPLE 41
N2-[6-(2-Benzoylhydrazino)-6-oxohexyl]-2-naphthalene-sulphonamide The expected product is obtained according to the process described in Example 40, in Step b replacing phenylhydrazine by phenylhydrazide.
Elemental microanalysis:

|  | C | H | N |
|---|---|---|---|
| % calculated | 62.79 | 5.69 | 9.56 |
| % found | 62.50 | 5.70 | 9.49 |

EXAMPLE 42
N2-[6-(2-Benzoylhydrazino)-6-oxohexyl]-2-(2-nitrophenyl)-sulphonamide The expected product is obtained according to the process described in Example 40, in Step a replacing 2-naphthylsulphonyl chloride by 2-nitrophenylsulphonyl chloride.
Melting point: 106° C.
Elemental microanalysis:

|  | C | H | N |
|---|---|---|---|
| % calculated | 52.53 | 5.10 | 12.89 |
| % found | 52.61 | 5.14 | 12.76 |

EXAMPLE 43
N2-({4-[(2-Phenylhydrazino)carbonyl]cyclohexyl}methyl)-2-naphthalenesulphonamide The expected product is obtained according to the process described in Example 40, in Step a replacing 6-aminocaproic acid by 4-(aminomethyl)cyclohexanecarboxylic acid.
Elemental microanalysis :($x^{1/2}H_2O$)

|  | C | H | N |
|---|---|---|---|
| % calculated | 64.50 | 6.27 | 9.41 |
| % found | 64.54 | 6.04 | 9.22 |

EXAMPLE 44
N2-({4-[(2-Benzoylhydrazino)carbonyl]cyclohexyl}methyl)-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by phenylhydrazide.

Elemental microanalysis: ($x^{1/2}H_2O$)

|  | C | H | N |
|---|---|---|---|
| % calculated | 63.22 | 5.90 | 8.85 |
| % found | 63.59 | 5.68 | 8.76 |

EXAMPLE 45
N2-[(4-{[2-(2-Indolylcarbonyl)hydrazino]carbonyl}cyclohexyl)-methyl]-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by 2-indolylcarbohydrazide.
Elemental microanalysis: ($x^{1/2}H_2O$)

|  | C | H | N |
|---|---|---|---|
| % calculated | 63.11 | 5.45 | 10.90 |
| % found | 63.11 | 5.72 | 11.10 |

EXAMPLE 46
N2-({4-[(2-Nicotinoylhydrazino)carbonyl]cyclohexyl}methyl)-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by 3-pyridinecarbohydrazide.
Melting point: 204–205° C.
Elemental microanalysis:

|  | C | H | N |
|---|---|---|---|
| % calculated | 61.76 | 5.57 | 12.01 |
| % found | 62.15 | 5.68 | 11.88 |

EXAMPLE 47
N2-{[4-({2-[2-(3-Indolyl)-acetyl]hydrazino}carbonyl)cyclohexyl]-methyl}-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by 3-indolylacetohydrazide.
Elemental microanalysis:

|  | C | H | N |
|---|---|---|---|
| % calculated | 62.61 | 5.77 | 10.44 |
| % found | 62.11 | 5.99 | 10.41 |

EXAMPLE 48
N1-({4-[(2-Phenylhydrazino)carbonyl]cyclohexyl}methyl)-1-benzylsulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride.

Melting point: 194–196° C.

Elemental microanalysis:

|  | C | H | N |
|---|---|---|---|
| % calculated | 61.99 | 6.50 | 10.84 |
| % found | 62.81 | 6.60 | 10.83 |

EXAMPLE 49

N1-({4-[(2-Benzoylhydrazino)carbonyl]cyclohexyl}methyl)-1-benzenesulphonamide

The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by phenylhydrazide.

Elemental microanalysis:

|  | C | H | N |
|---|---|---|---|
| % calculated | 60.70 | 6.06 | 10.11 |
| % found | 60.25 | 6.24 | 10.07 |

EXAMPLE 50

N1-({4-[(2-Nicotinoylhydrazino)carbonyl]cyclohexyl}methyl)-1-benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by 3-pyridinecarbohydrazide.

Melting point: 213–215° C.

Elemental microanalysis: ($x^{1/2}H_2O$)

|  | C | H | N |
|---|---|---|---|
| % calculated | 56.41 | 5.64 | 13.16 |
| % found | 56.45 | 5.74 | 13.56 |

EXAMPLE 51

N1-[(4-{[2-(4-Chlorophenyl)hydrazino]carbonyl}cyclohexyl)methyl]-1-benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by 4-chlorophenylhydrazine.

Elemental microanalysis:

|  | C | H | N |
|---|---|---|---|
| % calculated | 56.93 | 5.73 | 9.96 |
| % found | 56.91 | 5.82 | 9.86 |

EXAMPLE 52

N1-[(4-{2-(4-Chlorobenzoyl)hydrazino]carbonyl}cyclohexyl)methyl]-1-benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by 4-chlorophenylhydrazide.

Elemental microanalysis:

|  | C | H | N |
|---|---|---|---|
| % calculated | 56.01 | 5.33 | 9.33 |
| % found | 55.98 | 5.43 | 9.41 |

EXAMPLE 53

N1-({4-[(2-Phenylhydrazino)carbonyl]cyclohexyl}methyl)-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride.

Elemental microanalysis:

|  | C | H | N |
|---|---|---|---|
| % calculated | 55.54 | 5.59 | 12.95 |
| % found | 55.35 | 5.49 | 12.70 |

EXAMPLE 54

N1-({4-[(2-Benzoylhydrazino)carbonyl]cyclohexyl}methyl)-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride, and in Step b replacing phenylhydrazine by phenylhydrazide.

Elemental microanalysis: ($x^{1/2}H_2O$)

|  | C | H | N |
|---|---|---|---|
| % calculated | 53.72 | 5.15 | 11.93 |
| % found | 53.57 | 5.19 | 11.76 |

EXAMPLE 55

N1-{[4-(2-[2-(3-Indolyl)-acetyl]hydrazino}carbonyl)cyclohexyl]-methyl}-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride, and in Step b replacing phenylhydrazine by 3-indolylacetohydrazide.

Elemental microanalysis: ($x^{1/2}H_2O$)

|  | C | H | N |
|---|---|---|---|
| % calculated | 55.11 | 5.17 | 13.39 |
| % found | 55.13 | 5.14 | 13.35 |

EXAMPLE 56

N1-[(4-{2-(2-Indolylcarbonyl)hydrazino]carbonyl}cyclohexyl)-methyl]-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride, and in Step b replacing phenylhydrazine by 2-indolylcarbohydrazide.

Melting point: 249–251° C.

Elemental microanalysis:

|  | C | H | N |
|---|---|---|---|
| % calculated | 55.27 | 5.01 | 14.02 |
| % found | 55.02 | 5.28 | 14.39 |

EXAMPLE 57

N1-({4-[(2-Benzoylhydrazino)carbonyl]cyclohexyl}methyl)-1-(2-nitro-4-trifluoromethylphenyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitro-4-trifluoromethylphenylsulphonyl chloride, and in Step b replacing phenylhydrazine by phenylhydrazide.

Elemental microanalysis:

|  | C | H | N |
|---|---|---|---|
| % calculated | 50.00 | 4.36 | 10.61 |
| % found | 49.97 | 4.46 | 10.68 |

EXAMPLE 58

N1-({4-[(2-Phenylhydrazino)carbonyl]cyclohexyl}methyl)-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride.

Melting point: 192–194° C.

Elemental microanalysis:

|  | C | H | N |
|---|---|---|---|
| % calculated | 50.48 | 5.05 | 8.83 |
| % found | 50.38 | 5.15 | 8.69 |

EXAMPLE 59

N1-({4-[(2-Benzoylhydrazino)carbonyl]cyclohexyl}methyl)-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride, and in Step b replacing phenylhydrazine by phenylhydrazide.

Melting point: 251–253° C.

Elemental microanalysis:

|  | C | H | N |
|---|---|---|---|
| % calculated | 51.02 | 4.89 | 8.50 |
| % found | 50.47 | 4.92 | 8.34 |

EXAMPLE 60

N1-[(4-{[2-(4-Chlorophenyl)hydrazino]cyclohexyl}carbonyl)methyl]-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride, and in Step b replacing phenylhydrazine by 4-chlorophenylhydrazine.

Elemental microanalysis:

|  | C | H | N |
|---|---|---|---|
| % calculated | 47.96 | 4.63 | 8.39 |
| % found | 47.99 | 4.63 | 8.29 |

EXAMPLE 61

N1-[(4-{[2-(4-Chlorobenzoyl)hydrazino]cyclohexyl}carbonyl)methyl]-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride, and in Step b replacing phenylhydrazine by 4-chlorophenylhydrazide.

Elemental microanalysis:

|  | C | H | N |
|---|---|---|---|
| % calculated | 47.69 | 4.38 | 7.95 |
| % found | 47.78 | 4.45 | 8.05 |

EXAMPLE 62
N'-Phenyl-1-(phenylsulphonyl)perhydro-2-indolecarbohydrazide

Step a: 1-(Phenylsulphonyl)-2-perhydroindolecarboxylic acid 29.8 mmol (3.8 ml) of benzenesulphonyl chloride and 7.4 ml of 4M sodium hydroxide solution are added in succession to a solution, cooled to 0° C., of 29.6 mmol (5 g) of 2-perhydroindolecarboxylic acid in 7.4 ml of 4M NaOH. The reaction mixture is left at room temperature, with stirring, for 24 hours. The mixture is then rendered acidic to pH 2–3 and filtered. The resulting solid is washed with ether to yield the expected product.

Step b: N'-Phenyl-1-phenylsulphonyl)perhydro-2-indolecarbohydrazide

The expected product is obtained according to the process described in Step b of Example 1, using the compound described in the preceding Step as starting material.

Elemental microanalysis:

|  | C | H | N |
|---|---|---|---|
| % calculated | 63.16 | 6.27 | 10.53 |
| % found | 63.37 | 6.43 | 10.38 |

EXAMPLE 63
N'-(2-Indolylcarbonyl)-1-(phenylsulphonyl)perhydro-2-indole-carbohydrazide The expected product is obtained according to the process described in Example 62, in Step b replacing phenylhydrazine by 2-indolecarbohydrazide.

Melting point: 134–137° C.
Elemental microanalysis:

|  | C | H | N |
|---|---|---|---|
| % calculated | 61.80 | 5.58 | 12.02 |
| % found | 61.34 | 5.74 | 11.62 |

EXAMPLE 64
N'-Nicotinoyl-1-(phenylsulphonyl)perhydro-2-indolecarbohydrazide

The expected product is obtained according to the process described in Example 62, in Step b replacing phenylhydrazine by 3-pyridinecarbohydrazide.

Elemental microanalysis:

|  | C | H | N |
|---|---|---|---|
| % calculated | 58.88 | 5.61 | 13.08 |
| % found | 58.41 | 5.74 | 13.64 |

EXAMPLE 65
N2-({4-[(2-Phenylhydrazino)carbonyl]cyclohexyl}methyl)-1-naphthalenesulphonamide Step a: 6-(1-Naphthylsulphonyl)aminomethyl]cyclohexanecarboxylic acid The expected product is obtained according to the process described in Example 40, Step a, replacing 6-aminocaproic acid by 4-(aminomethyl)cyclohexanecarboxylic acid and using 1-naphthylsulphonyl chloride.

Step b: N2-({4-[(2-Phenylhydrazino)carbonyl]cyclohexyl}methyl)-1-naphthalene-sulphonamide The expected product is obtained according to the process described in Example 1, Step b, using the compound described in the preceding Step as starting material, and replacing phenylhydrazine by phenylhydrazide.

Elemental microanalysis:

|  | C | H | N |
|---|---|---|---|
| % calculated | 64.44 | 5.80 | 9.02 |
| % found | 64.59 | 5.96 | 8.76 |

EXAMPLE 66
N1-({4-[(2-Benzoylhydrazino)carbonyl]cyclohexyl}methyl)-1-(4-isopropylbenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-isopropylbenzenesulphonyl chloride, and in Step b replacing phenylhydrazine by phenylhydrazide.

Melting point: 232–236° C.
Elemental microanalysis:

|  | C | H | N |
|---|---|---|---|
| % calculated | 62.46 | 6.77 | 9.10 |
| % found | 62.32 | 7.20 | 9.18 |

EXAMPLE 67
N1-({4-[(2-Naphthoylhydrazino)carbonyl]cyclohexyl}methyl)-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl choride, and in Step b replacing phenylhydrazine by 2-naphthylhydrazide.

Melting point: 263–264° C.
Elemental microanalysis:

|  | C | H | N |
|---|---|---|---|
| % calculated | 58.81 | 5.13 | 10.97 |
| % found | 58.87 | 5.32 | 11.25 |

EXAMPLE 68
N1-({4-[(2-Benzoylhydrazino)carbonyl]cyclohexyl}methyl)-1-(3-nitrobenzene)sulphonamide The expected product is obtained according to the process described in Example 54, replacing 2-nitrobenzenesulphonyl chloride by 3-nitrobenzenesulphonyl chloride.

Melting point: 198–201° C.

Elemental microanalysis:

|  | C | H | N |
|---|---|---|---|
| % calculated | 51.69 | 4.92 | 11.48 |
| % found | 51.58 | 4.83 | 11.61 |

EXAMPLE 69
N1-({4-[(2-Phenylhydrazino)carbonyl]cyclohexyl}methyl)-1-(4-nitrobenzene)sulphonamide The expected product is obtained according to the process described in Example 53, replacing 2-nitrobenzenesulphonyl chloride by 4-nitrobenzenesulphonyl chloride.

Melting point: 200–201° C.
Elemental microanalysis:

|  | C | H | N |
|---|---|---|---|
| % calculated | 54.36 | 5.44 | 12.68 |
| % found | 53.99 | 5.33 | 12.46 |

EXAMPLE 70
N1-({4-[(2-Benzoylhydrazino)carbonyl]cyclohexyl}methyl)-1-(4-nitrobenzene)sulphonamide The expected product is obtained according to the process described in Example 54, replacing 2-nitrobenzenesulphonyl chloride by 4-nitrobenzenesulphonyl chloride.

Melting point: 262–264° C.
Elemental microanalysis:

|  | C | H | N |
|---|---|---|---|
| % calculated | 53.67 | 5.11 | 11.93 |
| % found | 53.68 | 5.21 | 11.96 |

EXAMPLE 71
N1-[(4-{[2-(4-Chlorophenyl)hydrazino]carbonyl}cyclohexyl)-methyl]-1-(4-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-nitrobenzenesulphonyl chloride, and in Step b replacing phenylhydrazine by 4-chlorophenylhydrazine.

Melting point: 211–213° C.
Elemental microanalysis:

|  | C | H | N |
|---|---|---|---|
| % calculated | 51.45 | 4.96 | 12.00 |
| % found | 51.52 | 5.12 | 11.81 |

EXAMPLE 72
N1-[(4-{[2-(4-Chlorobenzoyl)hydrazino]carbonyl}cyclohexyl)-methyl]-1-(4nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-nitrobenzenesulphonyl chloride, and in Step b replacing phenylhydrazine by 4-chlorophenylhydrazide.

Melting point: 272–273° C.
Elemental microanalysis:

|  | C | H | N |
|---|---|---|---|
| % calculated | 50.91 | 4.65 | 11.31 |
| % found | 50.89 | 4.76 | 11.29 |

EXAMPLE 73
N1-({4-[(2-(4-Phenylhydrazino)carbonyl]cyclohexyl}methyl)-1-(2-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride.

Melting point: 165–167° C.
Elemental microanalysis:

|  | C | H | N |
|---|---|---|---|
| % calculated | 51.46 | 5.14 | 9.01 |
| % found | 51.54 | 5.29 | 9.03 |

EXAMPLE 74
N1-({4-[(2-Benzoylhydrazino)carbonyl]cyclohexyl}methyl)-1-(2-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride, and in Step b replacing phenylhydrazine by phenylhydrazide.

Melting point: 231–232° C.
Elemental microanalysis:

|  | C | H | N |
|---|---|---|---|
| % calculated | 50.97 | 4.85 | 8.49 |
| % found | 51.11 | 4.98 | 8.51 |

EXAMPLE 75
N1-[(4-{[(2-(4-Chlorophenyl)hydrazino]carbonyl}cyclohexyl)-methyl]-1-(2-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride, and in Step b replacing phenylhydrazine by 4-chlorophenylhydrazine.

Elemental microanalysis:

|  | C | H | N |
|---|---|---|---|
| % calculated | 47.92 | 4.59 | 8.39 |
| % found | 48.15 | 4.73 | 8.37 |

EXAMPLE 76

N1-[(4-{[2-(4-Chlorophenyl)hydrazino]cyclohexyl}carbonyl)-methyl]-1-(2-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride, and in Step b replacing phenylhydrazine by 4-chlorophenylhydrazide.

Melting point: 263–264° C.

Elemental microanalysis:

|  | C | H | N |
|---|---|---|---|
| % calculated | 47.65 | 4.35 | 7.94 |
| % found | 47.65 | 4.44 | 7.87 |

EXAMPLE 77

N1-({4-[(2-Benzoylhydrazino)carbonyl]cyclohexyl)methyl)-1-(4-chlorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-chlorobenzenesulphonyl chloride, and in Step b replacing phenylhydrazine by phenylhydrazide.

Melting point: 254–256° C.

Elemental microanalysis:

|  | C | H | N |
|---|---|---|---|
| % calculated | 56.01 | 5.33 | 9.33 |
| % found | 56.00 | 5.22 | 9.24 |

EXAMPLE 78

N1-({4-[(2-Benzoylhydrazino)carbonyl]cyclohexyl}methyl)-1-(3,4-dichlorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 3,4-dichlorobenzenesulphonyl chloride, and in Step b replacing phenylhydrazine by phenylhydrazide.

Melting point: 251–252° C.

Elemental microanalysis:

|  | C | H | N |
|---|---|---|---|
| % calculated | 52.07 | 4.75 | 8.67 |
| % found | 51.91 | 5.32 | 8.71 |

EXAMPLE 79

N1-({4-[(2-Phenylhydrazino)carbonyl]cyclohexyl}methyl)-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride.

Melting point: 192–193° C.

Elemental microanalysis:

|  | C | H | N |
|---|---|---|---|
| % calculated | 59.19 | 5.92 | 10.36 |
| % found | 59.03 | 5.98 | 10.23 |

EXAMPLE 80

N1-({4-([(2-Benzoylhydrazino)carbonyl]cyclohexyl}methyl)-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride, and in Step b replacing phenylhydrazine by phenylhydrazide.

Melting point: 264–265° C.

Elemental microanalysis:

|  | C | H | N |
|---|---|---|---|
| % calculated | 58.13 | 5.54 | 9.69 |
| % found | 58.04 | 5.60 | 9.71 |

EXAMPLE 81

N1-[(4-{[2-(4-Chlorophenyl)hydrazino]carbonyl}cyclohexyl)-methyl]-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride, and in Step b replacing phenylhydrazine by 4-chlorophenylhydrazine.

Melting point: 216–217° C.
Elemental microanalysis:

|  | C | H | N |
|---|---|---|---|
| % calculated | 54.31 | 5.20 | 9.50 |
| % found | 54.39 | 5.22 | 9.45 |

EXAMPLE 82
N1-[(4-{[2-(4-Chlorobenzoyl)hydrazino]carbonyl}cyclohexyl)-methyl]-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride, and in Step b replacing phenylhydrazine by 4-chlorophenylhydrazide.

Melting point: 257–258° C.
Elemental microanalysis:

|  | C | H | N |
|---|---|---|---|
| % calculated | 53.85 | 4.92 | 8.98 |
| % found | 53.90 | 5.00 | 8.89 |

EXAMPLE 83
N1-(4-[(2-Benzoylhydrazino)carbonyl]cyclohexyl}methyl)-1-(4-methylbenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-methylbenzenesulphonyl chloride, and in Step b replacing phenylhydrazine by phenylhydrazide.

Elemental microanalysis:

|  | C | H | N |
|---|---|---|---|
| % calculated | 61.52 | 6.34 | 9.78 |
| % found | 61.71 | 6.32 | 9.67 |

EXAMPLE 84
N1-({4-[(2-Benzoylhydrazino)carbonyl]cyclohexyl}methyl)-1-(4-methoxybenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-methoxybenzenesulphonyl chloride, and in Step b replacing phenylhydrazine by phenylhydrazide.

Elemental microanalysis:

|  | C | H | N |
|---|---|---|---|
| % calculated | 59.25 | 6.06 | 9.43 |
| % found | 59.25 | 6.26 | 9.49 |

EXAMPLE 85
N1-({4-[(2-Benzoylhydrazino)carbonyl]cyclohexyl}methyl)-1-(3,4-dimethoxybenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 3,4-dimethoxybenzenesulphonyl chloride, and in Step b replacing phenylhydrazine by phenylhydrazide.

Melting point: 244–245° C.
Elemental microanalysis:

|  | C | H | N |
|---|---|---|---|
| % calculated | 57.02 | 5.99 | 8.68 |
| % found | 56.91 | 6.33 | 8.84 |

EXAMPLE 86
N1-({4-[(2-Benzoylhydrazino)carbonyl]cyclohexyl}methyl)-1-(4-acetylaminobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-(N-acetylamino)benzenesulphonyl chloride, and in Step b replacing phenylhydrazine by phenylhydrazide.

Elemental microanalysis:

|  | C | H | N |
|---|---|---|---|
| % calculated | 58.46 | 5.97 | 11.86 |
| % found | 58.29 | 6.04 | 11.73 |

EXAMPLE 87
N1-({4-[(2-Benzoylhydrazino)carbonyl]cyclohexyl}methyl)-1-(2-methylsulphonylbenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-(methylsulphonyl)benzenesulphonyl chloride, and in Step b replacing phenylhydrazine by phenylhydrazide.

Melting point: 193–194° C.
Elemental microanalysis:

|  | C | H | N |
|---|---|---|---|
| % calculated | 53.55 | 5.48 | 8.52 |
| % found | 53.17 | 5.74 | 8.49 |

EXAMPLE 88
N1-({4-[(2-Benzoylhydrazino)carbonyl]cyclohexyl}methyl)-1-(β-styrene)sulphonamide The expected product is obtained according to the process described in Example 40, in Step a replacing 6-aminocaproic acid by 4-(aminomethyl)cyclohexanecarboxylic acid and 2-naphthylsulphonyl chloride by (β-styrene)sulphonyl chloride, and in Step b replacing phenylhydrazine by phenylhydrazide.

Melting point: 208–209° C.
Elemental microanalysis:

|  | C | H | N |
|---|---|---|---|
| % calculated | 60.13 | 6.32 | 9.15 |
| % found | 60.06 | 6.45 | 9.05 |

EXAMPLE 89
N1-({4-[(2-Phenylhydrazino)carbonyl]cyclohexyl}methyl)-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride.
Melting point: 218–221° C.
Elemental microanalysis:

|  | C | H | N |
|---|---|---|---|
| % calculated | 54.89 | 5.84 | 10.67 |
| % found | 54.50 | 6.05 | 10.82 |

EXAMPLE 90
N1-({4-[(2-Benzoylhydrazino)carbonyl]cyclohexyl}methyl)-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride, and in Step b replacing phenylhydrazine by phenylhydrazide.
Melting point: 221–222° C.
Elemental microanalysis:

|  | C | H | N |
|---|---|---|---|
| % calculated | 52.96 | 5.34 | 9.76 |
| % found | 53.14 | 5.50 | 9.82 |

EXAMPLE 91
N1-[(4-{[2-(4-Chlorophenyl)hydrazino]carbonyl}cyclohexyl)-methyl]-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride, and in Step b replacing phenylhydrazine by 4-chlorophenylhydrazine.
Melting point: 193–194° C.
Elemental microanalysis:

|  | C | H | N |
|---|---|---|---|
| % calculated | 50.47 | 5.14 | 9.81 |
| % found | 50.50 | 5.27 | 9.73 |

EXAMPLE 92
N1-[(4-{[(2-(4-Chlorobenzoyl)hydrazino]carbonyl}cyclohexyl)-methyl]-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride, and in Step b replacing phenylhydrazine by 4-chlorophenylhydrazide.
Melting point: 237–239° C.
Elemental microanalysis:

|  | C | H | N |
|---|---|---|---|
| % calculated | 50.00 | 4.82 | 9.21 |
| % found | 49.93 | 4.97 | 9.37 |

EXAMPLE 93
N1-[6-Oxo-6-(2-phenylhydrazino)hexyl]-1-benzenesulphonamide

The expected product is obtained according to the process described in Example 40, replacing 2-naphthylsulphonyl chloride by benzenesulphonyl chloride.
Melting point: 123–124° C.
Elemental microanalysis:

|  | C | H | N |
|---|---|---|---|
| % calculated | 59.81 | 6.41 | 11.62 |
| % found | 59.92 | 6.58 | 11.52 |

EXAMPLE 94
N1-[6-(2-Benzoylhydrazino)-6-oxohexyl]-1-phenylsulphonamide

The expected product is obtained according to the process described in Example 40, replacing 2-naphthylsulphonyl chloride by benzenesulphonyl chloride, and phenylhydrazine by phenylhydrazide.
Melting point: 150° C.
Elemental microanalysis:

|  | C | H | N |
|---|---|---|---|
| % calculated | 58.59 | 5.95 | 10.79 |
| % found | 58.52 | 6.10 | 10.90 |

EXAMPLE 95
Benzyl N-[1-(4-methoxybenzyl)2-oxo-2-(2-phenylsulphonyl-hydrazino)ethyl]carbamate The expected product is obtained according to the process described in Example 1, in Step a replacing phenylalanine by O-methyltyrosine, and in Step b replacing phenylhydrazine by phenylsulphonylhydrazine.
Elemental microanalysis:

|  | C | H | N |
|---|---|---|---|
| % calculated | 59.63 | 5.18 | 8.70 |
| % found | 60.03 | 5.41 | 8.65 |

EXAMPLE 96
N1-[1-(4-Methoxybenzyl)-2-oxo-2-(2-phenylsulphonylhydrazino)-ethyl]-2-phenoxyacetamide The expected product is obtained according to the process described in Example 5, in Step a replacing phenylalanine by O-methyltyrosine, and in Step b replacing phenylhydrazine by phenylsulphonylhydrazine.

Elemental microanalysis:

|  | C | H | N |
|---|---|---|---|
| % calculated | 59.63 | 5.18 | 8.70 |
| % found | 59.52 | 5.06 | 8.59 |

EXAMPLE 97
N1-[1-Benzyl-2-oxo-2-(2-phenylsulphonylhydrazino) ethyl]-1-phenylsulphonamide The expected product is obtained according to the process described in Example 10, in Step a replacing 2-naphthylsulphonyl chloride by benzenesulphonyl chloride, and in Step b replacing phenylhydrazine by phenylsulphonylhydrazine.

Melting point: 182–183° C.
Elemental microanalysis:

|  | C | H | N |
|---|---|---|---|
| % calculated | 54.90 | 4.58 | 9.15 |
| % found | 54.70 | 4.79 | 8.91 |

EXAMPLE 98
N2-[1-Benzyl-2-oxo-2-(2-phenylsulphonylhydrazino) ethyl]-2-naphthylamide The expected product is obtained according to the process described in Example 1, in Step a replacing benzyl chloroformate by naphthoyl chloride, and in Step b replacing phenylhydrazine by phenylsulphonylhydrazine.

Elemental microanalysis:

|  | C | H | N |
|---|---|---|---|
| % calculated | 64.41 | 4.97 | 8.35 |
| % found | 63.95 | 5.01 | 8.29 |

EXAMPLE 99
1-[(4-Chlorophenyl)sulphonyl]-N'-phenylperhydro-2-indolecarbohydrazide The expected product is obtained according to the process described in Example 62, in Step a replacing benzenesulphonyl chloride by 4-chlorobenzenesulphonyl chloride.

Elemental microanalysis:

|  | C | H | N |
|---|---|---|---|
| % calculated | 58.13 | 5.54 | 9.68 |
| % found | 58.66 | 5.63 | 9.18 |

EXAMPLE 100
1-[(4-Chlorophenyl)sulphonyl]-N'-nicotinoyl-perhydro-2-indolecarbohydrazide The expected product is obtained according to the process described in Example 62, in Step a replacing benzenesulphonyl chloride by 4-chlorobenzenesulphonyl chloride, and in Step b replacing phenylhydrazine by 3-pyridinecarbohydrazide.

Elemental microanalysis:

|  | C | H | N |
|---|---|---|---|
| % calculated | 54.49 | 4.97 | 12.11 |
| % found | 54.54 | 5.21 | 12.32 |

EXAMPLE 101
1-[(2-Nitrophenyl)sulphonyl]-N'-phenylperhydro-2-indolecarbohydrazide The expected product is obtained according to the process described in Example 62, in Step a replacing benzenesulphonyl chloride by 2-nitrobenzenesulphonyl chloride.

Melting point: 86–89° C.
Elemental microanalysis:

|  | C | H | N |
|---|---|---|---|
| % calculated | 56.88 | 5.19 | 12.64 |
| % found | 56.78 | 5.49 | 12.26 |

EXAMPLE 102
N'-Benzoyl-1-[(2-nitrophenyl)sulphonyl]-perhydro-2-indolecarbohydrazide The expected product is obtained according to the process described in Example 62, in Step a replacing benzenesulphonyl chloride by 2-nitrobenzenesulphonyl chloride, and in Step b replacing phenylhydrazine by phenylhydrazide.

Melting point: 109–113° C.
Elemental microanalysis:

|  | C | H | N |
|---|---|---|---|
| % calculated | 55.93 | 5.08 | 11.86 |
| % found | 56.21 | 5.24 | 12.05 |

EXAMPLE 103
1-[(4-Chlorophenyl)sulphonyl]-N'-phenyl-2-pyrrolidine carbohydrazide The expected product is obtained according to the process described in Example 62, in Step a replacing perhydroindolecarboxylic acid by proline and benzenesulphonyl chloride by 4-chlorobenzenesulphonyl chloride.

Melting point: 133–135° C.
Elemental microanalysis:

|  | C | H | N |
|---|---|---|---|
| % calculated | 53.75 | 4.74 | 11.07 |
| % found | 53.94 | 4.89 | 10.81 |

EXAMPLE 104

N'-Benzoyl-1-[(4-chlorophenyl)sulphonyl]-2-pyrrolidine-carbohydrazide

The expected product is obtained according to the process described in Example 62, in Step a replacing perhydroindolecarboxylic acid by proline and benzenesulphonyl chloride by 4-chlorobenzenesulphonyl chloride, and in Step b replacing phenylhydrazine by phenyl-hydrazide.

Melting point: 171–172° C.

Elemental microanalysis:

|  | C | H | N |
|---|---|---|---|
| % calculated | 53.01 | 4.42 | 10.31 |
| % found | 53.26 | 4.53 | 10.36 |

EXAMPLE 105

1-[(4-Chlorophenyl)sulphonyl]-N'-nicotinoyl-2-pyrrolidine-carbohydrazide

The expected product is obtained according to the process described in Example 62, in Step a replacing perhydroindolecarboxylic acid by proline and benzenesulphonyl chloride by 4-chlorobenzenesulphonyl chloride, and in Step b replacing phenylhydrazine by 3-pyridinecarbohydrazide.

Melting point: 107–108° C.

Elemental microanalysis:

|  | C | H | N |
|---|---|---|---|
| % calculated | 49.94 | 4.16 | 13.71 |
| % found | 50.51 | 4.40 | 13.47 |

EXAMPLE 106

1-[(4-Chlorophenyl)sulphonyl]-N'-naphthyl-2-pyrrolidine carbohydrazide

The expected product is obtained according to the process described in Example 62, in Step a replacing perhydroindolecarboxylic acid by proline and phenylhydrazine by naphthylhydrazine.

Melting point: 178–180° C.

Elemental microanalysis:

|  | C | H | N |
|---|---|---|---|
| % calculated | 60.80 | 4.58 | 6.76 |
| % found | 60.78 | 4.73 | 6.79 |

EXAMPLE 107

N-({4-[(2-Benzoylhydrazino)carbonyl]cyclohexyl}methyl)-5-(dimethylamino)-1-napthalenesulphonamide The expected product is obtained according to the process described in Example 40, in Step a replacing 6-aminocaproic acid by 4-(aminomethyl)cyclohexanecarboxylic acid and 2-napthylsulphonyl chloride by 5-dimethylamino-1-naphthyl sulphonyle chloride and in step b replacing phenylhydrazine by phenylhydrazide. Elemental microanalysis:

|  | C | H | N |
|---|---|---|---|
| % calculated | 61.99 | 6.50 | 10.84 |
| % found | 62.81 | 6.60 | 10.83 |

EXAMPLE 108

4-Bromo-N-({4-[(2-{[4-(trifluoromethyl)-2-pyrimidinyl]carbonyl}hydrazino)carbonyl]cyclohexyl}methyl)benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride and in step b replacing phenylhydrazine by 4-(trifluorométhyl)-2-pyrimidinecarbohydrazide.

Melting point: 229–230° C.

Elemental microanalysis:

|  | C | H | N |
|---|---|---|---|
| % calculated | 41,16 | 4,15 | 12,64 |
| % found | 41,06 | 4,03 | 12,75 |

EXAMPLE 109

3,4-Dimethoxy-N-[(4-{[2-(3-pyridylcarbonyl)hydrazino]carbonyl}cyclohexyl)methyl]benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by 3,4-dimethoxybenzenesulphonyl chloride and in step b replacing phenylhydrazine by 3-pyridinecarbohydrazide.

Melting point: 211–212° C.

Elemental microanalysis:

|  | C | H | N |
|---|---|---|---|
| % calculated | 55,46 | 5,88 | 11,76 |
| % found | 55,43 | 5,75 | 11,86 |

EXAMPLE 110

N-({4-[(2-Benzoylhydrazino)carbonyl]cyclohexyl}methyl)-5-quinoleinesulphonamide

The expected product is obtained according to the process described in Example 40, in Step a replacing 6-aminocaproic acid by 4-(aminomethyl)cyclohexanecarboxylic acid and 2-naphthylsulphonyl chloride by 5-quinoleïnesulphonyl chloride and in step b replacing phenylhydrazine by phenylhydrazide.

Melting point: 215–216° C.
Elemental microanalysis:

|  | C | H | N |
|---|---|---|---|
| % calculated | 61,80 | 5,58 | 12,02 |
| % found | 61,69 | 5,66 | 12,13 |

EXAMPLE 111
N-{4-[(2-Benzoylhydrazino)carbonyl]benzyl}benzenesulphonamide

The expected product is obtained according to the process described in Example 40, in Step a replacing 6-aminocaproic acid by 4-(aminomethyl)benzoïc acid and 2-naphthylsulphonyl chloride by benzenesulphonyl chloride and in step b replacing phenylhydrazine by phenylhydrazide.

Melting point: 191–193° C.
Elemental microanalysis:

|  | C | H | N |
|---|---|---|---|
| % calculated | 61,54 | 4,64 | 10,26 |
| % found | 61,57 | 4,81 | 10,22 |

EXAMPLE 112
N2-{4-[(2-Benzoylhydrazino)carbonyl]benzyl}naphthalenesulphonamide The expected product is obtained according to the process described in Example 40, in Step a replacing 6-aminocaproic acid by 4-(aminomethyl)benzoïc acid and 2-naphthylsulphonyl chloride by benzenesulphonyl chloride and in step b replacing phenylhydrazine by phenylhydrazide.

Elemental microanalysis:

|  | C | H | N |
|---|---|---|---|
| % calculated | 65,29 | 4,57 | 9,14 |
| % found | 65,69 | 4,70 | 8,87 |

EXAMPLE 113
N-{4-[(2-Benzoylhydrazino)carbonyl]benzyl}-2-nitrobenzenesulphonamide The expected product is obtained according to the process described in Example 40, in Step a replacing 6-aminocaproic acid by 4-(aminomethyl)benzoïc acid and 2-naphthylsulphonyl chloride by 2-nitrobenzenesulphonyl chloride and in step b replacing phenylhydrazine by phenylhydrazide.

|  | C | H | N |
|---|---|---|---|
| % calculated | 55,45 | 3,96 | 12,32 |
| % found | 55,36 | 4,11 | 12,56 |

EXAMPLE 114
N-{4-[(2-Benzoylhydrazino)carbonyl]benzyl-}-4-bromobenzenesulphonamide The expected product is obtained according to the process described in Example 40, in Step a replacing 6-aminocaproic acid by 4-(aminomethyl)benzoïc acid and 2-naphthylsulphonyl chloride by 2-bromobenzenesulphonyl chloride and in step b replacing phenylhydrazine by phenylhydrazide.

Melting point: 208–210° C.
Elemental microanalysis:

|  | C | H | N |
|---|---|---|---|
| % calculated | 50,71 | 3,82 | 8,45 |
| % found | 50,85 | 3,61 | 8,42 |

PHARMACOLOGICAL STUDY

EXAMPLE A
Measurement of the in vitro affinity for NPY receptors

The capacity of the compounds of the invention to bind to NPY receptors was measured on various cell lines, each expressing one of the receptor sub-types studied. Competition binding experiments were carried out using the peptide [$^{125}$I]-PYY as radioligand at concentrations ranging from 15 to 65 pM. The non-specific fraction is measured in the presence of a concentration of 1 $\mu$M NPY. The cells are incubated for a period ranging from 1 to 2 hours depending upon the lines, and the radioactivity is collected after filtration over a GF/C filter treated with 0.1% PEI, before being measured.

Results:

The results are expressed as $IC_{50}$. The compounds of the invention appear to be capable of significantly displacing the reference ligand: the $IC_{50}$ values vary from a few nanomoles to some hundreds of nanomoles.

By way of example, the compound of Example 44 has an $IC_{50}$ of 14.5 DM for the $Y_5$ receptor.

EXAMPLE B
Measurement of the effect on food intake and weight development in the obese mouse The compounds of the invention were administered in vivo to the obese ob/ob mouse in order to evaluate their influence on food intake and weight development. The animals used are 13- to 18-week-old female ob/ob C57B1/6J mice. They are divided into groups each comprising 4 animals per cage, the cages being fitted with a grating floor, and the mice having free access to food. Before the experiments, the animals are conditioned for a period ranging from 2 to 3 weeks until their food consumption has stabilised. The experiments may be summarised as follows:

D–14 to D–7: conditioning
D–7 to D–3: measurement of the basal food intake
D0 to D+3: animals treated twice daily, the control groups being given the carrier
D0 to D+4: daily measurement of food intake and body weight The test products are dissolved, immediately before use, in water, 0.9% sodium chloride, propylene glycol or dimethyl sulphoxide, depending upon their solubility, and are administered intraperitoneally (IP), in a volume of 2.5 ml/kg.

The parameters measured are the weight of the feed troughs containing the food and the body weight.

Results:

The results are expressed as:

percentage variation in food intake under treatment compared with the basal food intake;

percentage variation in body weight between the first and last day of treatment.

By way of example, the results obtained with the compound of Example 44 are as follows:

| Product | Dose (mg/kg) | Food intake % variation (D1) Control | Food intake % variation (D1) Treated | Body weight % variation (D4/D0) |
|---|---|---|---|---|
| Example 44 | 5 | −25.3 | −75.2 | −6.0 |

EXAMPLE C

Acute toxicity study

The acute toxicity was evaluated after oral administration of increasing doses of the test compound to groups each comprising 8 mice (26±6 gramms). The animals were observed at regular intervals over the course of the first day and daily for the two weeks following treatment.

The compounds of the invention appear to be not very toxic at all.

EXAMPLE D

Pharmaceutical composition

Formulation for the preparation of 1000 tablets each comprising a dose of 10 mg

| | |
|---|---|
| Compound of Example 44 | 10 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

$$R\text{—}NH\text{—}A\text{—}CO\text{—}NH\text{—}NH\text{—}(W)_n\text{—}Z \quad (I)$$

wherein:

n is 0 or 1,

W represents —CO— or $S(O)_r$ wherein r is 0, 1 or 2,

Z represents a group selected from optionally substituted aryl and optionally substituted arylalkyl, R represents a group selected from:
- $Z_1$—T—CO—
- $Z_1$—O—T—CO—
- $Z_1$—T—O—CO—
- $Z_1$—T—$S(O)_q$— wherein:

$Z_1$ represents optionally substituted aryl or optionally substituted arylalkyl, T represents a σ bond, alkylene, alkenylene, or alkynylene, q represents an 0, 1 or 2, A represents alkylenecycloalkylene, cycloalkylenealkylene, alkylenecycloalkylenealkylene, alkylenearylene, arylenealkylene, alkylenearylenealkylene,

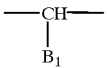

wherein $B_1$ represents optionally substituted aryl or optionally substituted arylalkyl, with the proviso that when simultaneously n is 0, A represents

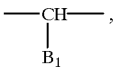

$B_1$ being benzyl, and Z represents optionally substituted phenyl, then R is other than benzoyl, its enantiomers, diastereoisomers, and pharmaceutically-acceptable an addition salts thereof with an pharmaceutically-acid or base, it being understood that:

the term "alkyl" denotes a linear or branched alkyl group having 1 to 6 carbon atoms, the term "alkylene" denotes a linear or branched bivalent alkylene radical containing from 1 to 6 carbon atoms, unless indicated otherwise, the term "alkenylene" denotes a linear or branched bivalent alkylene radical containing 2 to 6 carbon atoms and 1 to 3 double bonds, unless indicated otherwise, the term "alkynylene" denotes a linear or branched alkylene bivalent radical containing 2 to 6 carbon atoms and 1 to 3 triple bonds, unless indicated otherwise, the term "aryl" denotes phenyl, naphthyl, dihydronaphthyl or tetrahydronaphthyl, and the term "arylene" denotes a bivalent radical of the same type, the term "alkylenecycloalkylene" represents —$A_1$—$A_2$—, the term "cycloalkylene-alkylene" represents —$A_2$—$A_1$—, and the term "alkylenecycloalllylene-alkylene" represents —$A_1$—$A_2$—$A_1$, the term "alkylenearylene" represents —$A_1$—$A_3$—, the term "arylenealkylene" represents —$A_3$—$A_1$—, the term "alkylenearylenealkylene" represents —$A_1$—$A_3$—$A_1$—, wherein $A_1$ is alkylene as defined hereinbefore, $A_2$ is $(C_4-C_8)$cycloalkylene, and $A_3$ is arylene as defined hereinbefore, the expression "optionally substituted" applied to the terms "aryl" or, "arylalkyl", indicates that those groups maybe substituted on their cyclic moiety by 1 to 5 identical or different substituents selected from linear or branched $(C_1-C_6)$alkyl, linear or branched $(C_1-C_6)$ alkoxy, halogen, hydroxy, perhalo-$(C_1-C_6)$alkyl in which the alkyl moiety is linear or branched, nitro, linear or branched $(C_1-C_6)$acyl, linear or branched $(C_1-C_6)$alkylsulphonyl, and amino (amino being optionally substituted by one or two linear or branched $(C_1-C_6)$alkyl and/or linear or branched $(C_1-C_6)$acyl).

2. A compound of claim 1 wherein W represents —CO—.

3. A compound of claim 1 wherein W represents —$SO_2$—.

4. A compound of claim 1 wherein R represents $Z_1$—T—CO, T being alkylene or a bond.

5. A compound of claim 1 wherein R represents $Z_1$—O—T—CO, T being alkylene or a bond.

6. A compound of claim 1 wherein R represents $Z_1$—T—O—CO, T being alkylene or a bond.

7. A compound of claim 1 wherein R represents $Z_1$—T—$S(O)_q$—, T being alkylene or a bond.

8. A Compound of claim 1 wherein Z represents an optionally substituted aryl, its enantiomers, diastereoisomers, and addition salts thereof with a pharmaceutically-acceptable acid or base.

9. A compound of claim 1 wherein A represents

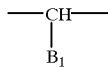

wherein $B_1$ is optionally substituted arylalkyl.

10. A compound of claim 1 wherein A represents alkylenecycloalkylene.

11. A compound of claim 1 wherein A represents alkylenearylene.

12. A compound of claim 1 selected from those wherein W represents —CO—, Z represents a group selected from optionally substituted aryl, R represents a grouping selected from $Z_1$—T—CO—, $Z_1$—O—T—CO—, $Z_1$—T—O—CO—, and $Z_1$—T—S(O)$_q$—, wherein $Z_1$ is optionally substituted aryl, T represents alkylene, and q is 2, and A represents alkylenecycloalkylene,

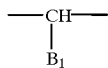

wherein $B_1$ is optionally substituted arylalkyl, and its enantiomers, diastereoisomers, and addition salts thereof with a pharmaceutically-acceptable acid or base.

13. A compound of claim 1 which is selected from N2-({4-[(2-benzoylhydrazino)-carbonyl]cyclohexyl}methyl)-2-naphthalenesulphonamide, and its enantiomers, diastereoisomers, and addition salts thereof with a pharmaceutically-acceptable acid or base.

14. A compound of claim 1 which is selected from N1-({4-[(2-benzoylhydrazino)-carbonyl]cyclohexyl}methyl)-1-(2-nitrobenzene)sulphonamide, and its enantiomers, diastereoisomers, and addition salts thereof with a pharmaceutically-acceptable acid or base.

15. A compound of claim 1 which is selected from N1-[1-benzyl-2-oxo-2-(2-phenylhydrazino)ethyl]-1-(4-chlorobenzene)sulphonamide, and addition salts thereof with a pharmaceutically-acceptable acid or base.

16. A pharmaceutical composition useful as a Neuropeptide Y receptor ligand comprising as active principle an effective amount of a compound as claimed in claim 1, together with with one or more pharmaceutically-acceptable excipients or vehicles.

17. A method for treating a living animal body afflicted with a condition requiring a neuropeptide Y receptor ligand and associated with eating behaviour disorders and/or energy balance disorders selected from diabetes, obesity, bulimia, and anorexia nervosa, comprising the step of administering to the living body an amount of a compound of claim 1 which is effective for alleviation of said condition.

18. A method for treating a living animal body afflicted with a condition requiring a neuropeptide Y receptor ligand and selected from arterial hypertension, anxiety, depression, epilepsy, sexual dysfunctions and sleep disorders, comprising the step of administering to the living body an amount of a compound of claim 1 which is effective for alleviation of said condition.

* * * * *

UNITED STATES PATENT AND TRADEMARK OFFICE
CERTIFICATE OF CORRECTION

PATENT NO. : 6,172,108 B1
DATED : January 9, 2001
INVENTOR(S) : A.M. Vega et al.

It is certified that error appears in the above-identified patent and that said Letters Patent is hereby corrected as shown below:

Column 3,
Line 15, "AI" should read -- $A_1$ --.

Column 4,
Line 41, "B," should read -- $B_1$ --.

Column 5,
Line 7, insert -- (V) -- in the upper right corner of the formula.

Column 9,
Line 29, "(2-phenylhydrazinoethyl]" should read -- (2-phenylhydrazino) ethyl] --.

Column 10,
Line 44, "(2-phenylkydrazine)" should read -- (2-phenylhydrazine) --.

Column 12,
Line 51, "- (24 indolylcarbonyl)" should read -- (2-indolylcarbonyl) --.

Column 23,
Line 14, The sentence beginning "29.8" should begin a new paragraph.
Line 21, "- phenylsulphonyl)perhydro-2-" should read -- ( -phenylsulphonyl)perhydro-2 --.

Column 29,
Line 1, "Melting point: 216-21 7°C" should read -- Melting point: 216-217º C --.

Column 35,
Line 67, "Elemental microanalysis:" should be moved to the top of Column 36 as new line 2.

Column 36,
Line 1, insert -- Melting point: 201-203º C --.

Column 38,
Line 41, "14.5 DM" should read -- 14.5 nM --.

Column 39,
Line 63, delete the word "an".

UNITED STATES PATENT AND TRADEMARK OFFICE
CERTIFICATE OF CORRECTION

PATENT NO. : 6,172,108 B1
DATED : January 9, 2001
INVENTOR(S) : A.M. Vega et al.

It is certified that error appears in the above-identified patent and that said Letters Patent is hereby corrected as shown below:

Column 40,
Line 17, delete the word "an".
Line 18, delete the word "pharmaceutically-".
Line 23, delete the word "from".
Line 36, "alkylenecycloalllylene-" should read -- alkylenecycloalkylene- --.

Signed and Sealed this

Tenth Day of August, 2004

JON W. DUDAS
*Acting Director of the United States Patent and Trademark Office*